US009322935B2

(12) United States Patent
Ronda et al.

(10) Patent No.: US 9,322,935 B2
(45) Date of Patent: Apr. 26, 2016

(54) TERBIUM BASED DETECTOR SCINTILLATOR

(75) Inventors: Cornelis Reinder Ronda, Aachen (DE);
Norbert Conrads, Raeren (BE);
Henning Ohland, Aachen (DE);
Herbert Schreinemacher, Baesweiler (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 341 days.

(21) Appl. No.: 14/234,639

(22) PCT Filed: Jul. 3, 2012

(86) PCT No.: PCT/IB2012/053372
§ 371 (c)(1),
(2), (4) Date: Jan. 24, 2014

(87) PCT Pub. No.: WO2013/014557
PCT Pub. Date: Jan. 31, 2013

(65) Prior Publication Data
US 2014/0177783 A1 Jun. 26, 2014

Related U.S. Application Data

(60) Provisional application No. 61/512,452, filed on Jul. 28, 2011.

(51) Int. Cl.
*G01T 1/20* (2006.01)
*C09K 11/77* (2006.01)
(Continued)

(52) U.S. Cl.
CPC ........... *G01T 1/2006* (2013.01); *C09K 11/7771* (2013.01); *G01N 23/046* (2013.01); *G01T 1/2023* (2013.01); *G21K 4/00* (2013.01)

(58) Field of Classification Search
CPC ............... G01N 21/6408; G21K 4/00; G21K 2201/061; G21K 2004/06; G01T 1/20; G01T 1/2018
See application file for complete search history.

(56) References Cited

U.S. PATENT DOCUMENTS 3,974,389 A 8/1976 Ferri et al.
6,340,436 B1 1/2002 Yamada et al.
(Continued)

FOREIGN PATENT DOCUMENTS

CN 1111603 A 11/1995
EP 0235387 A2 9/1987
(Continued)

OTHER PUBLICATIONS

Nakamura, R.; Improvements in the X-ray Characteristics of Gd2O2S:Pr Ceramic Scintillators; 1999; Journal of the American Ceramic Society; 82(9):2407-2410.
(Continued)

*Primary Examiner* — Hoon Song

(57) ABSTRACT

An imaging system (100) includes a radiation source (110) and a radiation sensitive detector array (116), which includes a scintillator array (118) and a photosensor array (120) optically coupled to the scintillator array, wherein the scintillator array includes $Gd_2O_2S:Pr,Tb,Ce$. A method includes detecting radiation with a radiation sensitive detector array (116) of an imaging system (100), wherein the radiation sensitive detector array includes a $Gd_2O_2S:Pr,Tb,Ce$ based scintillator array (118). A radiation sensitive detector array (116) includes a scintillator array (118) and a photosensor array (120) optically coupled to the scintillator array, wherein the scintillator array includes $Gd_2O_2S:Pr,Tb,Ce$, and an amount of $Tb^{3+}$ in the $Gd_2O_2S:Pr,Tb,Ce$ is equal to or less than two hundred mole parts per million.

20 Claims, 4 Drawing Sheets

(51) Int. Cl.
  *G01T 1/202* (2006.01)
  *G21K 4/00* (2006.01)
  *G01N 23/04* (2006.01)

(56) References Cited

U.S. PATENT DOCUMENTS

2008/0179566 A1* 7/2008 Ronda .................... C04B 35/547
  252/301.4 S
2010/0320391 A1* 12/2010 Antonuk ............. H01L 27/1462
  250/366
2012/0228509 A1* 9/2012 Kusayama ............ G01T 1/2002
  250/361 R

FOREIGN PATENT DOCUMENTS

| EP | 0825161 A1 | 2/1998 |
| WO | 2006111900 A2 | 10/2006 |
| WO | 2007004099 A1 | 1/2007 |
| WO | 2007083248 A1 | 7/2007 |

OTHER PUBLICATIONS

Nakamura R., et al.; Development of Gd2O2S: Pr, Ce, F Ceramic Scintillator for X-ray CT; 2001; Memoirs of Shonan Institute of Technology; 35(1)19-28.

Nikl, M.; Scintillation detectors for x-rays; 2006; Measurement Science and Technology; 17:R37-R54.

* cited by examiner

TERBIUM BASED DETECTOR SCINTILLATOR

CROSS REFERENCE TO RELATED APPLICATIONS

This application is a national filing of PCT application Serial No. PCT/IB2012/053372, filed Jul. 3, 2012, published as WO 2013/014557 A1 on Jan. 31, 2013, which claims the benefit of U.S. provisional application Ser. No. 61/512,452 filed Jul. 28, 2011, which is incorporated herein by reference.

FIELD OF THE INVENTION

The following generally relates to a radiation sensitive imaging detector with a terbium ($Tb^{3+}$) based scintillator array and is described with particular application to computed tomography (CT). However, the following is also applicable to other imaging modalities.

BACKGROUND OF THE INVENTION

A computer tomography (CT) scanner includes an x-ray tube and a detector array. The x-ray tube is supported by a rotating gantry, which rotates about an examination region, thereby rotating the x-ray tube about the examination region. A detector array is located opposite the x-ray tube, across the examination region. The x-ray tube emits radiation that traverses the examination region (and a portion of a subject or object therein) and illuminates the detector array. The detector array detects radiation traversing the examination region and generates a signal indicative thereof. A reconstructor reconstructs the signal, generating three dimensional volumetric imaging data. A data processor can process the three dimensional volumetric imaging data and generate one or more images based thereon.

A conventional detector array has included a scintillator based detector array. A typical scintillator based detector array includes a scintillator array optically coupled to a photodiode array. By way of example, a conventional scintillator based detector array has included a gadolinium oxysulfide (GOS) based (e.g., $Gd_2O_2S$:Pr,Ce) scintillator array optically coupled to a silicon (Si) photodiode array. The radiation traversing the examination region illuminates the scintillator array, which absorbs the x-ray photons and, in response, emits optical photons, which are indicative of the absorbed x-ray photons. The photodiode array detects the optical photons and generates an electrical signal indicative of the detected optical photons. The reconstructor reconstructs this signal.

$Gd_2O_2S$:Pr,Ce based scintillator arrays have had a light yield or output of about 40,000 photons/MeV, with an afterglow suitable for CT applications. Generally, the light output corresponds to conversion efficiency, or the ability to convert absorbed x-ray photons into optical photons. Thus, there is an unresolved need for scintillator arrays with higher conversion efficiency and light output, with afterglow suitable for CT applications.

SUMMARY OF THE INVENTION

Aspects of the present application address the above-referenced matters and others.

According to one aspect, an imaging system includes a radiation source and a radiation sensitive detector array, which includes a scintillator array and a photosensor array optically coupled to the scintillator array, wherein the scintillator array includes $Gd_2O_2S$:Pr,Tb,Ce.

According to another aspect, a method includes detecting radiation with a radiation sensitive detector array of an imaging system, wherein the radiation sensitive detector array includes a $Gd_2O_2S$:Pr,Tb,Ce based scintillator array (118)s.

According to another aspect, a radiation sensitive detector array includes a scintillator array and a photosensor array optically coupled to the scintillator array, wherein the scintillator array includes $Gd_2O_2S$:Pr,Tb,Ce, and an amount of $Tb^{3+}$ in the $Gd_2O_2S$:Pr,Tb,Ce is equal to or less than two hundred parts per million.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
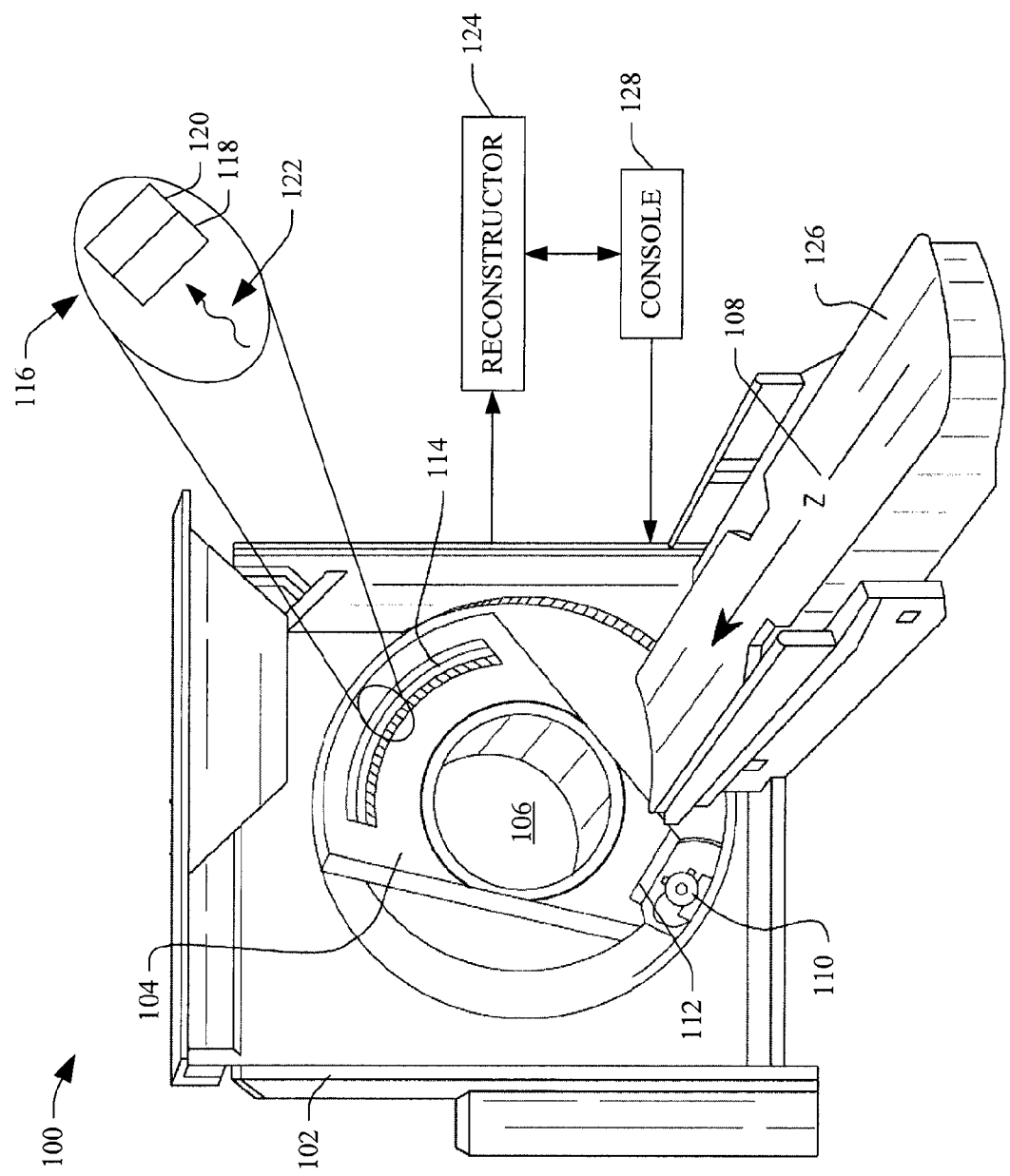
FIG. 1 schematically illustrates an example imaging system with a detector array including a terbium based scintillator array.

FIG. 1 illustrates an imaging system 100 such as a computed tomography (CT) scanner.

The imaging system 100 includes a stationary gantry 102 and a rotating gantry 104, which is rotatably supported by the stationary gantry 102. The rotating gantry 104 rotates around an examination region 106 about a longitudinal or z-axis 108.

A radiation source 110, such as an x-ray tube, is supported by and rotates with the rotating gantry 104, and emits radiation towards the examination region 106.

A source collimator 112 collimates the emitted radiation to form a generally cone, fan, wedge, or otherwise shaped radiation beam that traverses the examination region 106 and a portion of an object or subject therein.

A radiation sensitive detector array 114 is affixed to the rotating gantry 104 and subtends an angular arc, across from the radiation source 110, opposite the examination region 106. The illustrated detector array 114 includes at least one detector module 116 with a scintillator array 118 optically coupled to a photosensor array 120. The scintillator array 118 absorbs x-ray photons 122 and, in response, emits optical photons (e.g., visible light or ultraviolet radiation), which are indicative of the absorbed x-ray photons 122. The photosensor array 120 detects the optical photons and generates an electrical (current or voltage) signal indicative of the detected optical photons.

As described in greater detail below, the illustrated scintillator array 118 includes $Gd_2O_2S$:Pr,Tb,Ce in which the amount of terbium ($Tb^{3+}$) in the $Gd_2O_2S$:Pr,Tb,Ce increases light output (i.e., photon-to-light conversion efficiency), relative to a configuration without the terbium ($Tb^{3+}$), while satisfying a predetermined afterglow (or light decay) threshold. In the illustrated embodiment, the photosensor array 120 is coupled to a back of the scintillator array 118. In another embodiment, the photosensor array 120 is coupled to a side of the scintillator array 118. In addition, suitable scintillator arrays include composite and ceramic scintillator array, such as those respectively described in US201000032578 and US2010/00167909, which are incorporated in their entirety by reference herein.

A reconstructor 124 reconstructs the signal and generates volumetric image data indicative of the examination region 106 and the portion of the subject or object therein.

A subject support 126, such as a couch, supports an object or subject in the examination region 106. The support 126 is movable along the x, y and z-axes in coordination with the rotation of the rotating gantry 104 to facilitate helical, axial, or other desired scanning trajectories.

A general purpose computing system serves as an operator console 128, which includes human readable output devices such as a display and input devices such as a keyboard and/or mouse. Software resident on the console 128 allows the operator to control an operation of the system 100, for example, by allowing the operator to initiate scanning, etc.

As briefly discussed above, the illustrated scintillator array 118 is co-doped with an amount of $Tb^{3+}$ which increases light output, relative to a configuration without the $Tb^{3+}$, while satisfying a predetermined afterglow threshold.

Figure 2:
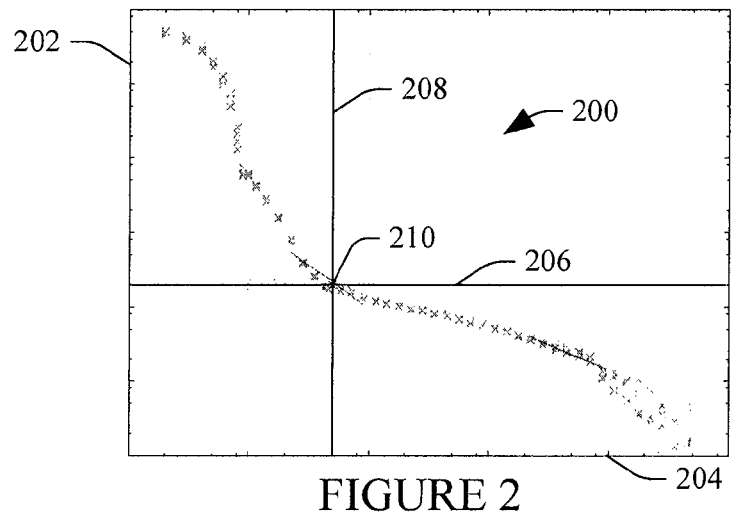
FIGS. 2, 3, and 4 graphically illustrate time dependent emission intensity curves of $Gd_2O_2S$:Pr,Tb,Ce after x-ray excitation respectively for three different amounts of $Tb^{3+}$ in connection with a predetermined light output threshold of 200 ppm and a predetermined threshold time of 5 ms.
Figure 3:
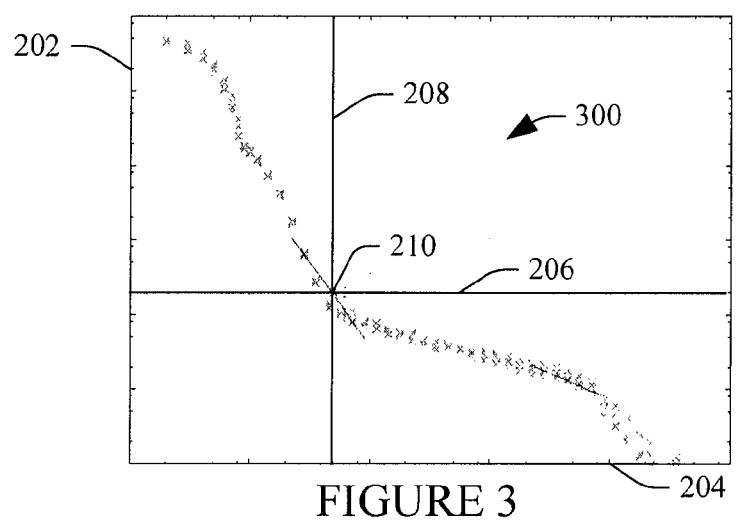
Figure 4:
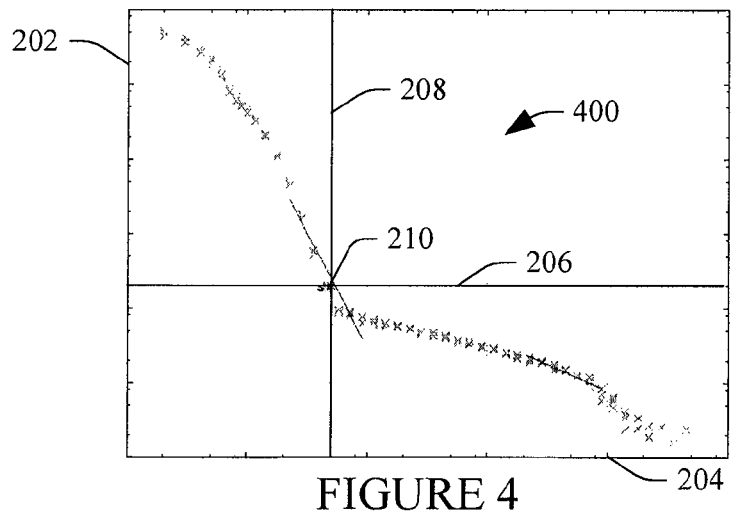

FIGS. 2, 3 and 4 graphically illustrate time dependent emission intensity curves 200, 300 and 400 of $Gd_2O_2S$:Pr,Tb,Ce after x-ray excitation is stopped respectively for three different amounts of $Tb^{3+}$. In FIGS. 2, 3 and 4, a y-axis 202 represents normalized light intensity in a logarithmic scale and an x-axis 204 represents time in a logarithmic scale. For these examples, a light output threshold 206 is set at 200 parts per million (ppm) at a time threshold 208 of 5 milliseconds (ms). In other embodiments, the thresholds 206 and/or 208 can be can different, including larger or smaller.

In FIG. 2, the amount of $Tb^{3+}$ in the $Gd_2O_2S$:Pr,Tb,Ce is approximately 10 mole ppm, in FIG. 3, the amount of $Tb^{3+}$ in the $Gd_2O_2S$:Pr,Tb,Ce is approximately 50 mole ppm, and in FIG. 4, the amount of $Tb^{3+}$ in the $Gd_2O_2S$:Pr,Tb,Ce is approximately 200 mole ppm. From FIGS. 2, 3 and 4, the light output threshold 206 is satisfied by all three amounts of $Tb^{3+}$ (10, 50 and 200 ppm) at the time threshold 208, as shown by the curves 200, 300 and 400, as the curves 200, 300 and 400 all fall at or below the light output threshold 206 at an intersection 210 of the light output threshold 206 and at the time threshold 208.

The above is summarized in TABLE 1 below.

TABLE 1

| | Light yield for a given amount of $Tb^{3+}$ at 5 ms. | | |
|---|---|---|---|
| Figure Number | $Tb^{3+}$ (mole ppm) | Light yield (photon/MeV) | Normalized afterglow (ppm) at 5 ms |
| FIG. 1 | 10 | 46,700 | 100 |
| FIG. 2 | 50 | 49,200 | 100 |
| FIG. 3 | 200 | 53,000 | 200 |

From FIGS. 2, 3 and 4 and TABLE 1, for the light output threshold 206 of 200 ppm, an amount of $Tb^{3+}$ up to 200 mole ppm can be used. With this amount, the light output of the scintillator array 118 is approximately 53,000 photon/MeV. This represents an increase of light output of approximately 33% relative to the 40,000 photon/MeV light output of the scintillator discussed in the background. Higher increases in light yield, for example, by more than 35% such as up to 50%, can be achieved while still complying with CT time dependent light intensity specifications. For amounts of $Tb^{3+}$ over 200 ppm, the $Tb^{3+}$ begins to dominate the afterglow behavior, increasing the effective short afterglow of the scintillator, due to the relatively slow emission of $Tb^{3+}$ in $Gd_2O_2S$.

Also from FIGS. 2, 3 and 4 and TABLE 1, where the light output threshold 206 is instead 100 ppm or less, an amount of $Tb^{3+}$ up to 50 mole ppm can be used. With this amount, the light output of the scintillator array 118 is approximately 49,200 photon/MeV. This represents an increase of light output of approximately 23% relative to the 40,000 photon/MeV light output of the scintillator discussed in the background. From FIGS. 2, 3 and 4 and TABLE 1, where the light output threshold 206 is greater than 200 ppm, an amount of $Tb^{3+}$ greater than 200 mole ppm can be used.

Generally, as $Gd_2O_2S$:Pr,Ce does not show losses due to concentration quenching nor to thermal quenching of the luminescence, very likely the transfer of energy from host lattice states to $Pr^{3+}$ states has efficiency smaller than unity, consequently this energy is not used to generate light to be used subsequently in the CT procedures. With $Gd_2O_2S$:Pr,Tb, Ce, the additional amount of $Tb^{3+}$ provides an additional radiative recombination or energy scavenging channel. However, as $Tb^{3+}$ has a much slower intrinsic decay time, this sets an upper limit to the $Tb^{3+}$ concentration. Too high a $Tb^{3+}$ concentrations results in too high relative light intensities as a function of time, compared to the light intensity immediately after the X-ray pulse as only a fraction of the photons is generated by $Tb^{3+}$ ions, of course also $Pr^{3+}$ ions contribute to the photon generation process. So the relative contributions of $Tb^{3+}$ and $Pr^{3+}$ have to be tuned carefully so as not to degrade properties of $Gd_2O_2S$:Pr,Ce, such as the very small afterglow.

FIGS. 2, 3, and 4 include a single threshold point, namely, the intersection 210, as criteria to determine a maximum amount of $Tb^{3+}$ which can be added to the scintillator material to increase light output. It is to be appreciated that the amount of $Tb^{3+}$ to add can be determined based on more than a single threshold point. An example of this is shown in connection with FIGS. 5, 6, and 7. Similar to FIGS. 2, 3 and 4, in FIGS. 5, 6, and 7 the y-axis 202 represents normalized light intensity in a logarithmic scale and the x-axis 204 represents time in a logarithmic scale.

Figure 5:
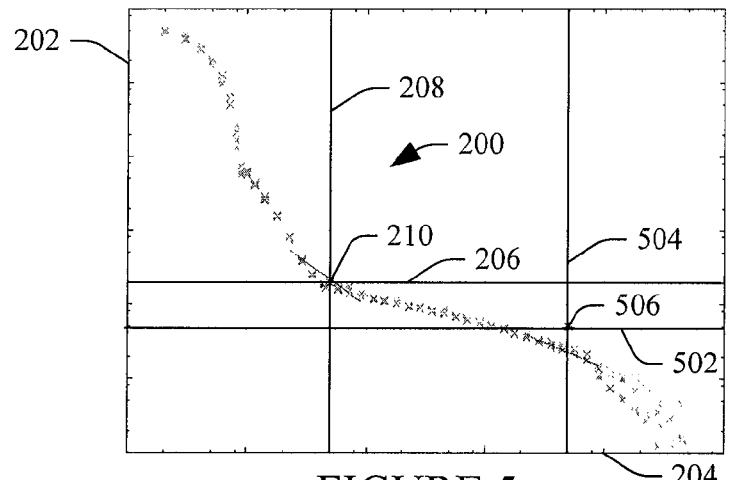
FIGS. 5, 6, and 7 graphically illustrate time dependent emission intensity curves of $Gd_2O_2S$:Pr,Tb,Ce after x-ray excitation respectively for three different amounts of $Tb^{3+}$ in connection with predetermined light output thresholds of 200 and 50 ppm and predetermined threshold times of 5 and 500 ms.
Figure 6:
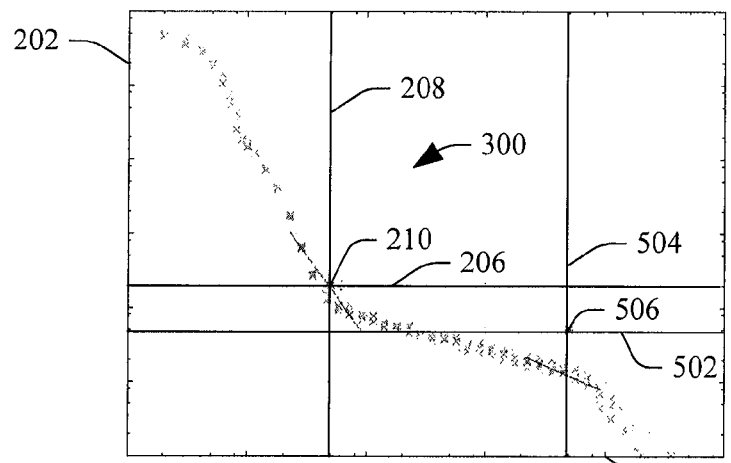
Figure 7:
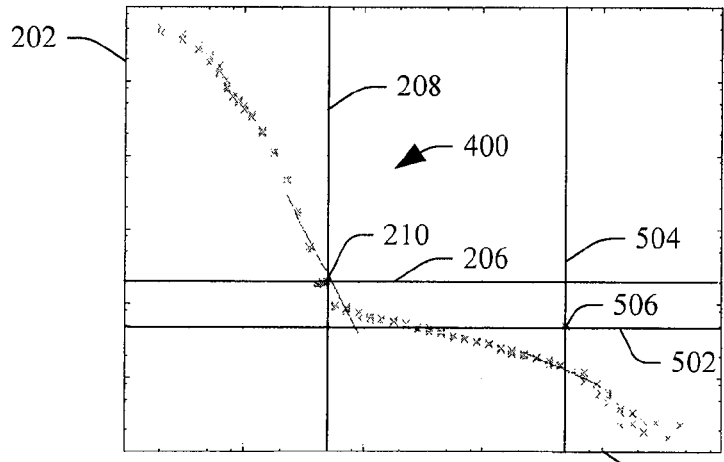

From FIGS. 5, 6 and 7, a second light output threshold 502 of 50 ppm is satisfied by all three amounts of $Tb^{3+}$ (10, 50 and 200 mole ppm) at a second time threshold 504 of 500 ms, as shown by the curves 200, 300 and 400, as the curves 200, 300 and 400 all fall below the second light output threshold 502 at an intersection 506 of the second light output threshold 502 and at the second time threshold 504. In other examples, still more light output and/or time thresholds can be used, where appropriate.

Figure 8:
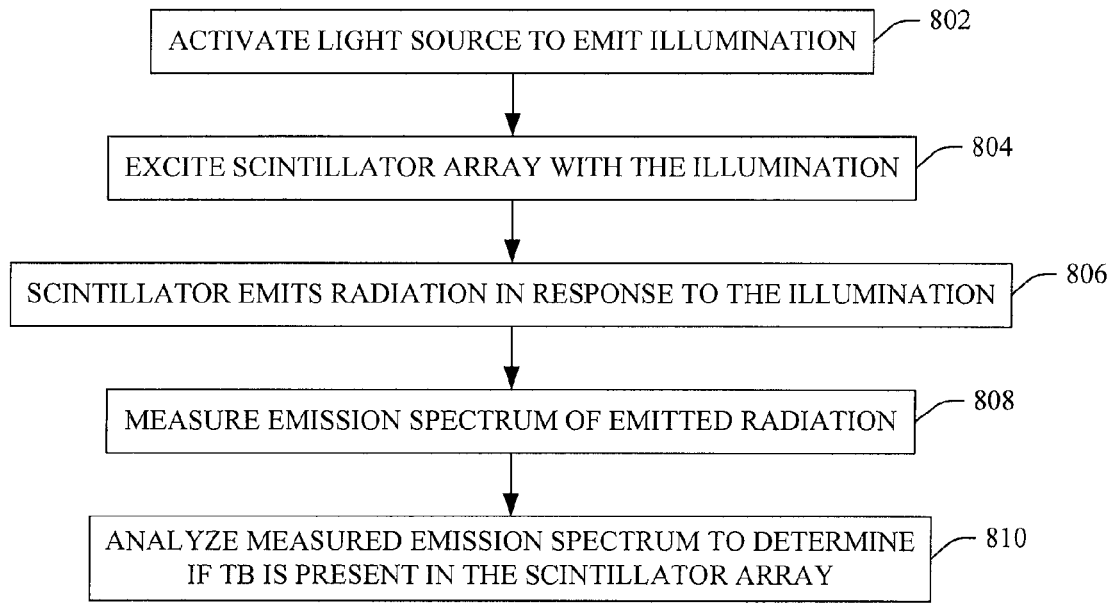
FIG. 8 illustrates an example method for detecting a presence of $Tb^{3+}$ in a scintillator.

FIG. 8 illustrates a method for detecting a presence of $Tb^{3+}$ in a scintillator.

It is to be appreciated that the ordering of the following acts is for illustrative purposes and not limiting. As such, the ordering may be different, including concurrent acts. Moreover, one or more of the acts can be omitted and/or one or more acts can be included.

At 802, a light source is activated to illuminate the scintillator array 118. An example of a suitable light source includes a light source that emits 254 nm light.

At 804, the scintillator array 118 is excited by the illumination.

At 806, the scintillator array 118, in response to being illuminated, emits characteristic radiation.

At 808, the emission spectrum of the emitted radiation is measured.

At 810, the measured emission spectrum is analyzed to determine whether $Tb^{3+}$ is present. In one instance, this includes identifying a presence of emissions lines below 490 nm, where $Pr^{3+}$ does not emit in this material, and which are indicative of a presence of $Tb^{3+}$. Such lines include lines at about 450 nm, 410 nm and 380 nm. A high emission intensity line at 545 nm may also be observed. Other approaches are also contemplated herein.

Figure 9:
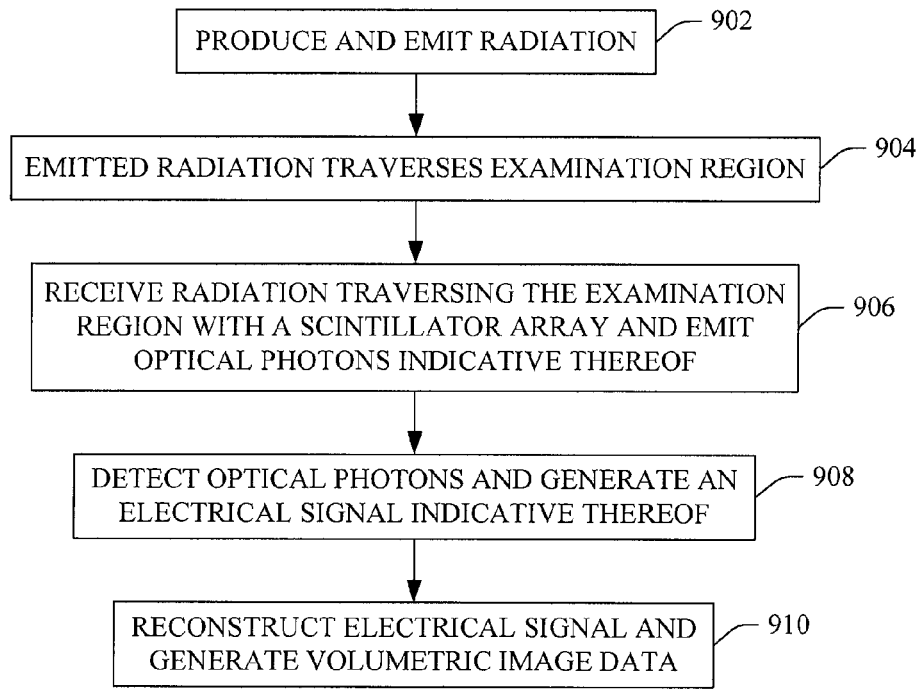
FIG. 9 illustrates an example imaging method employing a detector array with a scintillator array having $Gd_2O_2S$:Pr,Tb, Ce.

FIG. 9 illustrates an imaging method.

It is to be appreciated that the ordering of the follow acts is for illustrative purposes and not limiting. As such, the ordering may be different, including concurrent acts. Moreover, one or more of the acts can be omitted and/or one or more acts can be included.

At 902, radiation is produced and emitted by the radiation source 110.

At 904, the emitted radiation traverses the examination region 106 and a portion of a subject or object therein.

At 906, radiation traversing the examination region 106 and the portion of the subject or object therein is received by the scintillator array 118, which absorbs the radiation and emits optical photons indicative of the received radiation.

As discussed herein, in one instance, the scintillator 118 includes an amount of $Tb^{3+}$ to achieve a desired light output with a desired light decay. For example, as shown herein, for a light output of less than 200 ppm at or after 5 ms, less than 200 ppm of $Tb^{3+}$ can be used to increase the light intensity by approximately 33% relative to a configuration in which the $Tb^{3+}$ is not added.

At 908, the optical photons are detected via the photosensor array 120, which generates an electrical signal indicative of the detected radiation.

At 910, the electrical signal is reconstructed, thereby generating volumetric image data indicative of the examination region 106 and the portion of the subject or object therein.

The above may be implemented via one or more processors executing one or more computer readable instructions encoded or embodied on computer readable storage medium such as physical memory which causes the one or more processors to carry out the various acts and/or other functions and/or acts. Additionally or alternatively, the one or more processors can execute instructions carried by transitory medium such as a signal or carrier wave.

Although the above describes determining the amount Tb for a scintillator based on a combination of light output and decay time thresholds, in another instance, the amount Tb is based on a predetermined ratio of Tb and Pr, Tb and Ce, Tb and Pr and Ce, and/or Tb to other elements of the scintillator. In yet another instance, the amount Tb is based solely on a predetermined light output threshold. The approximate relative Light Yield (LY) (e.g., a number between 0 and 1) can be determine by: [N(Pr)+25N(Tb)]/[N(Pr)+25N(Tb)+25N(Ce)+400], where N is in mole ppm. The absolute light yield is then given by: 45000*[N(Pr)+25N(Tb)]/[N(Pr)+25N(Tb)+25N(Ce)+400]. In still another instance, the amount Tb is based on another predetermined characteristic.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

What is claimed is:

1. An imaging system, comprising:
   a radiation source; and
   a radiation sensitive detector array, including:
      a scintillator array; and
      a photosensor array optically coupled to the scintillator array, wherein the scintillator array includes $Gd_2O_2S$:Pr,Tb,Ce, wherein the amount of the $Tb^{3+}$ is equal to or less than fifty mole parts per million.

2. The imaging system of claim 1, wherein the $Gd_2O_2S$:Pr,Tb,Ce includes $Tb^{3+}$ in an amount in which a light output of the scintillator is below a predetermined light output threshold at a predetermined decay time.

3. The imaging system of claim 2, wherein the amount of the $Tb^{3+}$ is equal to or less than ten mole parts per million.

4. The imaging system of claim 1, wherein the light output is approximately 53,000 photon/MeV.

5. The imaging system of claim 1, wherein the scintillator array includes a composite material.

6. The imaging system of claim 1, wherein the scintillator array includes a ceramic material.

7. The imaging system of claim 1, wherein a light efficiency of the scintillator array is approximately thirty three percent greater than a configuration in which the scintillator array does not include the $Tb^{3+}$.

8. The imaging system of claim 1, wherein the imaging system is a computed tomography scanner.

9. A method, comprising:
   detecting radiation with a radiation sensitive detector array of an imaging system, wherein the radiation sensitive detector array includes a $Gd_2O_2S$:Pr,Tb,Ce based scintillator array and the amount of the $Tb^{3+}$ is equal to or less than ten mole parts per million.

10. The method of claim 9, wherein the $Gd_2O_2S$:Pr,Tb,Ce includes $Tb^{3+}$ in an amount in which a light output of the scintillator is below a predetermined light output threshold at a predetermined decay time.

11. The method of claim 10, wherein the amount of the $Tb^{3+}$ is equal to or less than ten mole parts per million.

12. The method of claim 9, wherein the light output is approximately 46,700 photon/MeV.

13. The method of claim 9, wherein the scintillator array includes one of a composite material or a ceramic material.

14. The method of claim 9, wherein a light efficiency of the scintillator array is approximately thirty three percent greater than a configuration in which the scintillator array does not include the $Tb^{3+}$.

15. The method of claim 9, wherein the imaging system is a computed tomography scanner.

16. A radiation sensitive detector array, comprising:
   scintillator array; and
   a photosensor array optically coupled to the scintillator array, wherein the scintillator array includes $Gd_2O_2S$:Pr,Tb,Ce, and an amount of $Tb^{3+}$ in the $Gd_2O_2S$:Pr,Tb,Ce is equal to or less than ten mole parts per million.

17. The detector array of claim 16, wherein $Gd_2O_2S$:Pr,Tb,Ce includes $Tb^{3+}$ in an amount in which a light output of the scintillator is below a predetermined light output threshold at a predetermined decay time.

18. The detector array of claim 16, wherein the scintillator array includes a composite material or a ceramic material.

19. The detector array of claim 16, wherein a light efficiency of the scintillator array is approximately thirty three percent greater than a configuration in which the scintillator array does not include the $Tb^{3+}$.

20. The detector array of claim 16, wherein the imaging system is a computed tomography scanner.

\* \* \* \* \*